(12) United States Patent
Ridler et al.

(10) Patent No.: US 10,751,524 B2
(45) Date of Patent: Aug. 25, 2020

(54) INTERFERENCE SUPPRESSION IN TISSUE-STIMULATING PROSTHESES

(71) Applicant: Cochlear Limited, Macquarie University, NSW (AU)

(72) Inventors: Oliver Ridler, Sydney (AU); Adam Hersbach, East Melbourne (AU)

(73) Assignee: COCHLEAR LIMITED, Macquarie University, NSW (AU)

( * ) Notice: Subject to any disclaimer, the term of this patent is extended or adjusted under 35 U.S.C. 154(b) by 66 days.

(21) Appl. No.: 15/623,798

(22) Filed: Jun. 15, 2017

(65) Prior Publication Data

US 2018/0361151 A1    Dec. 20, 2018

(51) Int. Cl.
*A61N 1/36* (2006.01)
*H04R 25/00* (2006.01)
*A61N 1/02* (2006.01)
*A61N 1/08* (2006.01)
*A61N 1/05* (2006.01)

(52) U.S. Cl.
CPC ............... *A61N 1/025* (2013.01); *A61N 1/08* (2013.01); *A61N 1/36036* (2017.08); *A61N 1/36125* (2013.01); *A61N 1/36189* (2013.01); *H04R 25/453* (2013.01); *H04R 25/505* (2013.01); *A61N 1/0541* (2013.01); *H04R 25/305* (2013.01); *H04R 25/606* (2013.01); *H04R 2225/43* (2013.01); *H04R 2225/67* (2013.01); *H04R 2420/01* (2013.01)

(58) Field of Classification Search
CPC ............ A61N 1/36036; A61N 1/36038; H04R 25/505
See application file for complete search history.

(56) References Cited

U.S. PATENT DOCUMENTS

| | | | |
|---|---|---|---|
| 5,091,952 A * | 2/1992 | Williamson | H04R 25/453 381/318 |
| 5,201,006 A | 4/1993 | Weinrich | |
| 5,621,802 A * | 4/1997 | Harjani | H04R 25/453 381/312 |
| 6,347,148 B1 * | 2/2002 | Brennan | H04R 25/453 381/312 |
| 6,611,600 B1 * | 8/2003 | Leber | H04R 25/453 379/406.08 |
| 7,574,012 B2 | 8/2009 | Eggers et al. | |

(Continued)

OTHER PUBLICATIONS

International Search Report and Written Opinion in corresponding International Appln. No. PCT/IB2018/054159, dated Oct. 4, 2018.

*Primary Examiner* — William J Levicky
(74) *Attorney, Agent, or Firm* — Edell, Shapiro & Finnan, LLC (57) ABSTRACT

Presented herein are techniques for suppressing electrical interference caused by a feedback path(s) between an output channel and an input channel of an implantable medical device. In particular, the output channel carries stimulation signals that can pass through the feedback path(s) and appear in the input channel, thereby causing interference with any input signals carried by the input channel. The implantable medical device is configured to determine characteristics of the feedback and subsequently use the feedback characteristics to generate feedback compensation signals for application to the input channel.

29 Claims, 7 Drawing Sheets

(56) References Cited

U.S. PATENT DOCUMENTS

| | | | |
|---|---|---|---|
| 8,170,248 B2* | 5/2012 | Hersbach | H04R 25/453 |
| | | | 257/416 |
| 2002/0094100 A1* | 7/2002 | Kates | H04R 25/453 |
| | | | 381/318 |
| 2003/0053647 A1* | 3/2003 | Kates | H04R 25/453 |
| | | | 381/318 |
| 2004/0264706 A1 | 12/2004 | Ray et al. | |
| 2007/0167671 A1 | 7/2007 | Miller, III | |
| 2008/0095389 A1* | 4/2008 | Theverapperuma | H04R 25/453 |
| | | | 381/318 |
| 2010/0232634 A1* | 9/2010 | Boldt | H04R 25/453 |
| | | | 381/318 |
| 2011/0249846 A1 | 10/2011 | Natarajan | |
| 2011/0249847 A1* | 10/2011 | Salvetti | H04R 25/453 |
| | | | 381/318 |
| 2012/0232333 A1 | 9/2012 | Miller, III | |
| 2013/0170660 A1* | 7/2013 | Kristensen | H04R 25/305 |
| | | | 381/60 |
| 2014/0369537 A1* | 12/2014 | Pontoppidan | H04R 25/305 |
| | | | 381/314 |
| 2016/0183010 A1 | 6/2016 | Natarajan | |
| 2017/0246456 A1* | 8/2017 | Tyler | A61N 1/0551 |
| 2018/0063654 A1* | 3/2018 | Kuriger | H04R 25/453 |

* cited by examiner

INTERFERENCE SUPPRESSION IN TISSUE-STIMULATING PROSTHESES

BACKGROUND

Field of the Invention

The present invention relates generally to interference suppression in tissue-stimulating prostheses.

Related Art

Implantable medical device systems, which include one or more implantable components, have provided a wide range of therapeutic benefits to recipients over recent decades. The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

There are several types of implantable medical devices that operate by delivering electrical stimulation (current stimulation) to the nerves, muscle or other tissue fibers of a recipient. These implantable medical device, sometimes referred to herein as implantable tissue-stimulating prostheses, typically deliver current stimulation to compensate for a deficiency in the recipient. For example, tissue-stimulating auditory/hearing prostheses are often proposed when a recipient experiences sensorineural hearing loss due to, for example, the absence or destruction of the cochlear hair cells that transduce acoustic signals into nerve impulses or when a recipient experiences sensorineural hearing loss due to damage to the auditory nerve.

SUMMARY

In one aspect, a method is provided. The method comprises: detecting the presence of one or more feedback paths between an output channel and an input channel of an implantable medical device, wherein the one or more feedback paths enables feedback, which comprises a portion of stimulation signals on the output channel, to appear in the input channel; determining a feedback transfer function associated with the one or more feedback paths; and based on the feedback transfer function, cancelling feedback appearing in the input channel in response to the delivery of stimulation signals via the output channel.

In one aspect, a method is provided. The method comprises: detecting the presence of at least one feedback path between an output channel and an input channel of an implantable medical device; generating a model of the at least one feedback path; delivering stimulation signals to a recipient of the implantable medical device via the output channel, wherein the stimulation signals are delivered at a stimulation frequency; and using the stimulation frequency of the stimulation signals and the model of the one or more feedback paths to identify feedback appearing at the input channel in response to the delivery of the stimulation signals.

In another aspect, a tissue-stimulating prosthesis is provided. The tissue-stimulating prosthesis comprises: at least one input channel including an implantable sensor and one or more associated conductors; at least one output channel including a stimulation component and one or more associated conductors; and an interference suppression module configured to: detect, on the least one input channel, feedback generated by the at least one output channel via at least one feedback path, and determine real-time feedback compensation for application at the at least one input channel, wherein application of the real-time feedback compensation is configured to cancel the feedback at the at least one input channel.

In another aspect, an implantable medical device method is provided. The implantable medical device comprises at least one input channel and at least one output channel configured to carry input signals and stimulation signals, respectively, and the method comprises: detecting, at the at least one input channel, feedback from the at least one output channel via one or more feedback paths, where the feedback comprises a portion of the stimulation signals; determining feedback compensation for application at the at least one input channel, wherein application of the feedback compensation is configured to cancel the feedback from the at least one of the one or more output channels; and applying the feedback compensation at the at least one input channel.

BRIEF DESCRIPTION OF THE DRAWINGS

Embodiments of the present invention are described herein in conjunction with the accompanying drawings, in which.

DETAILED DESCRIPTION

Embodiments of the present invention are generally directed to techniques for suppressing interference caused by a feedback path between an output channel and an input channel of an implantable medical device. In particular, the output channel carries stimulation signals that can pass through the feedback path and appear in the input channel as feedback (i.e., interference at the input channel). The implantable medical device is configured to determine characteristics of the feedback and subsequently use the feedback characteristics to generate feedback compensation signals for application to the input channel.

Merely for ease of illustration, the techniques presented herein are primarily described with reference to one type of implantable tissue-stimulating prosthesis, namely a cochlear implant. However, it is to be appreciated that the techniques presented herein may be used in other implantable tissue-stimulating prostheses that include, for example, auditory brainstem stimulators, implantable pacemakers, defibrillators, functional electrical stimulation devices, pain relief stimulators, visual prostheses, other neural or neuromuscular stimulators, etc.

Figure 1A:
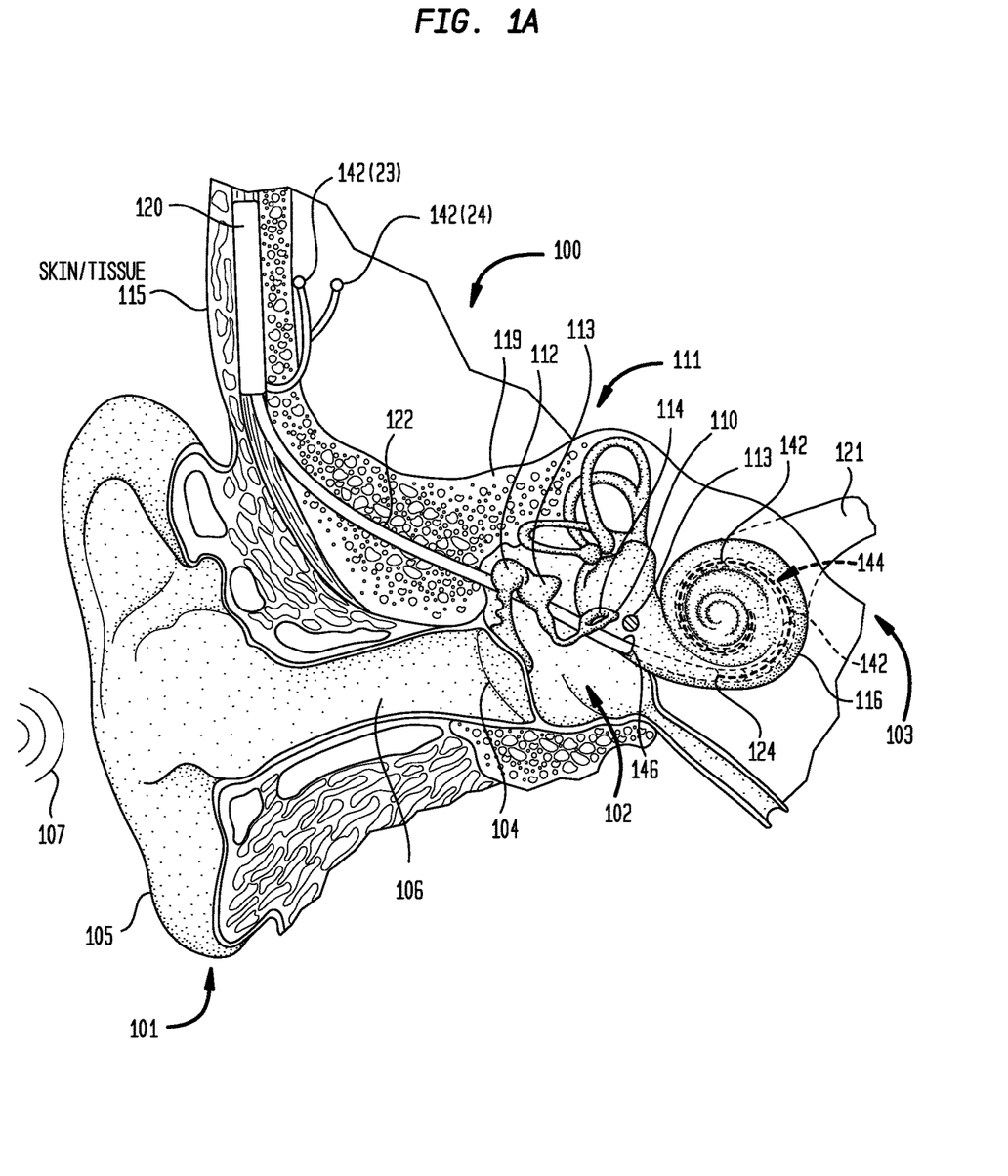
FIG. 1A is a schematic diagram illustrating a cochlear implant, in accordance with certain embodiments presented herein.
Figure 1B:
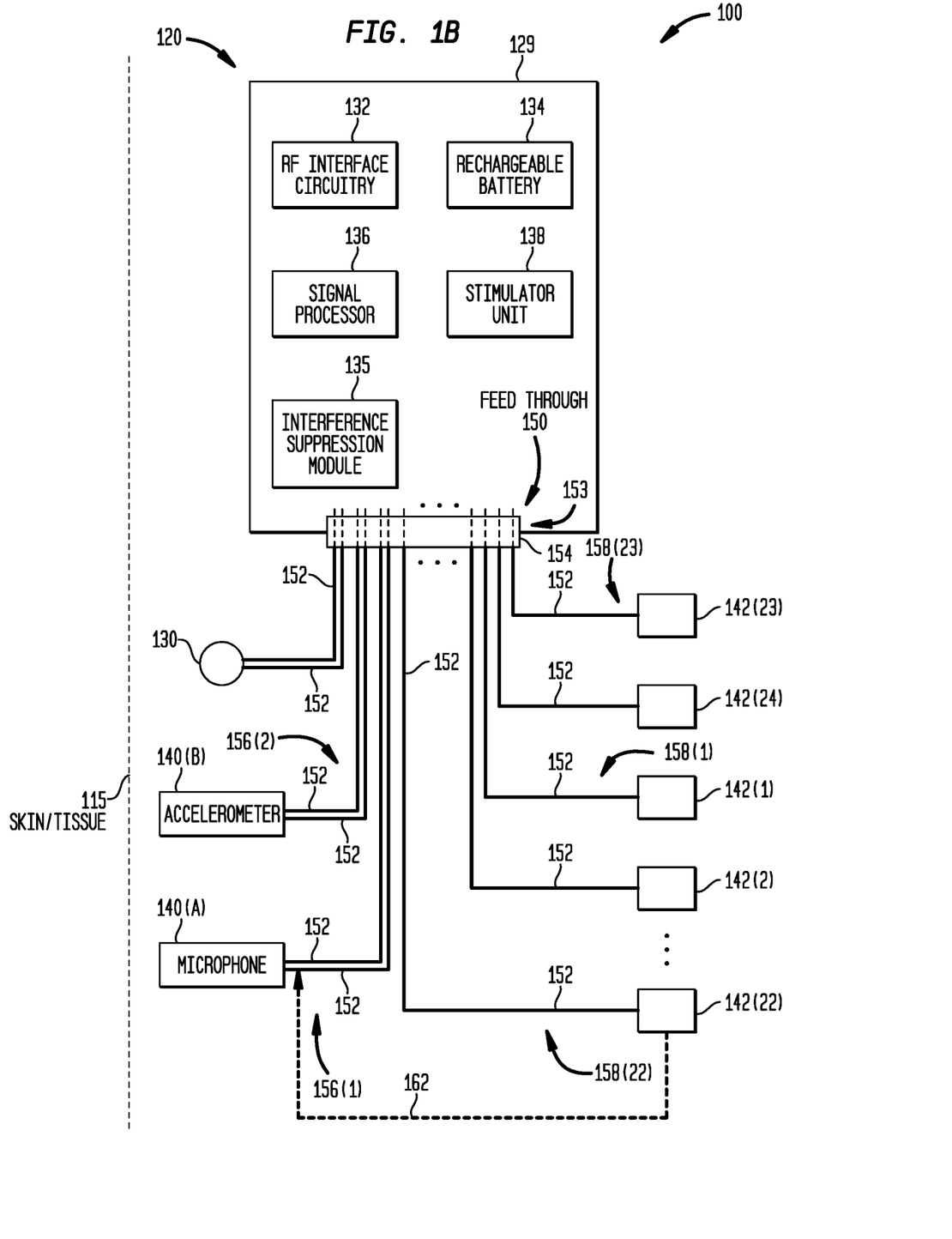
FIG. 1B is a block diagram of the cochlear implant of FIG. 1A.

FIG. 1A is schematic diagram of an exemplary cochlear implant 100 configured to implement embodiments of the present invention, while FIG. 1B is a block diagram of the cochlear implant 100. For ease of description, FIGS. 1A and 1B will be described together.

Shown in FIG. 1A is an outer ear 101, a middle ear 102 and an inner ear 103 of the recipient. In a fully functional human hearing anatomy, the outer ear 101 comprises an auricle 105 and an ear canal 106. Sound signals 107, sometimes referred to herein as acoustic sounds or sound waves, are collected by the auricle 105 and channeled into and through the ear canal 106. Disposed across the distal end of the ear canal 106 is a tympanic membrane 104 which vibrates in response to the sound signals (i.e., sound waves) 107. This vibration is coupled to the oval window or fenestra ovalis 110 through three bones of the middle ear 102, collectively referred to as the ossicular chain or ossicles 111 and comprising the malleus 112, the incus 113 and the stapes 114. The ossicles 111 of the middle ear 102 serve to filter and amplify the sound signals 107, causing oval window 110 to vibrate. Such vibration sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

As noted above, sensorineural hearing loss may be due to the absence or destruction of the cochlea hair cells, which transduce acoustic signals into nerve impulses. One treatment for such hearing loss is a cochlear implant, such as cochlear implant 100 shown in FIGS. 1A and 1B, which bypasses the cochlear hair cells and delivers stimulation (e.g., electrical stimulation) directly to the cochlea nerve cells.

In the illustrative embodiment of FIGS. 1A and 1B, the cochlear implant 100 is a totally implantable cochlear implant, meaning that all components of the cochlear implant are configured to be implanted under skin/tissue 115 of a recipient. Because all components of cochlear implant 100 are implantable, the cochlear implant operates, for at least a finite period of time, without the need of an external device. An external device can be used to, for example, charge an internal power source (battery) of the cochlear implant 100.

The cochlear implant 100 comprises an implant body or main module 120, a lead region 122, and an elongate intra-cochlear stimulating assembly 124. The implant body 120 comprises a hermetically sealed housing 129 in which radio frequency (RF) interface circuitry 132 (sometimes referred to as a transceiver unit), at least one rechargeable battery 134, an interference suppression module 135, a signal processor 136, and a stimulator unit 138 are disposed. The housing 129 operates as a protective barrier between the electrical components within the housing (e.g., in RF interface circuitry 132, battery 134, etc.) and the recipient's tissue and bodily fluid. For ease of illustration, electrical connections between the components within housing 129 have been omitted from FIG. 1B.

The implant body 120 also comprises one or more electrical components located outside (external to) the housing 129. The electrical components located outside the housing 129 include an internal/implantable coil 130, implantable sensors/transducers 140(A) and 140(B), and the elongate intra-cochlear stimulating assembly 124.

The RF interface circuitry 132 is connected to the implantable coil 130 and, generally, a magnet (not shown) is fixed relative to the implantable coil 130. Implantable coil 130 is typically a wire antenna coil comprised of multiple turns of electrically insulated single-strand or multi-strand platinum or gold wire. In general, the implantable coil 130 and the RF interface circuitry 132 enable the transfer of power and/or data from an external device to the cochlear implant 100. However, it is to be appreciated that various types of energy transfer, such as infrared (IR), electromagnetic, capacitive and inductive transfer, may be used to transfer power and/or data from an external device to a cochlear implant 100 and, as such, FIG. 1B illustrates only one example arrangement.

Elongate stimulating assembly 124 is configured to be at least partially implanted in cochlea 116 and extends through an opening in the cochlea 116 (e.g., cochleostomy 146, oval window 110, the round window 113, etc.). The stimulating assembly 124 has a proximal end connected to stimulator unit 138 via lead region 122 that extends through mastoid bone 119. Lead region 122 couples the stimulating assembly 124 to implant body 120 and, more particularly, to stimulator unit 138.

The stimulating assembly 124 includes a plurality of longitudinally spaced intra-cochlear electrical stimulating contacts (electrodes) 142 that can be selectively used to deliver current to the cochlea 116. The stimulating contacts 142 collectively form an intra-cochlear contact/electrode array 144 that, in the example of FIG. 1B, comprises twenty-two (22) stimulating contacts, labeled as contacts 142(1)-142(22). Although FIG. 1B illustrates the use of twenty-two stimulating contacts, is to be appreciated that different numbers, arrangements, etc., of intra-cochlear contacts may be used in alternative embodiments.

Also shown in FIGS. 1A and 1B are two reference contacts 142(23) and 142(24). The reference contacts 142(23) and 142(24) are located outside of the cochlear 116 and can also be used to deliver current to the recipient. Since the reference contacts 142(23) and 142(24) are located outside of the cochlea 116, the reference contacts are sometimes referred to as extra-cochlear electrodes (ECEs).

As noted above, the cochlear implant 100 comprises two implantable sensors 140(A) and 140(B). In the illustrative embodiment of FIG. 1B, the implantable sensor 140(A) is a "sound" sensor/transducer that is primarily configured to detect/receive external acoustic sounds (e.g., an implantable microphone), while the implantable sensor 140(B) is a "vibration" sensor that is primarily configured to detect/receive internal body noises (e.g., another implantable microphone or an accelerometer which is configured to be more sensitive to body noises than it is to external acoustic sound signals). As used herein, body noises (BNs) are undesirable sounds induced by the body that are propagated primarily as vibration, such as breathing, scratching, rubbing, noises associated with the movement of the head, chewing, etc. Own voice (OV) (i.e., when the recipient speaks) is a particular case of body noise since the sound is transmitted both through air conduction and bone conduction (i.e., skull vibrations). In certain own voice instances, most of these sound propagates through the skull bones and produce accelerations at the implantable sensors. For ease of description, embodiments presented herein will be primarily described with reference to the use of an implantable microphone 140(A) as the sound sensor and an accelerometer 140(B) as the vibration sensor. However, it is to be appreciated that these specific implementations are non-limiting and that embodiments of the present invention may be used with different types of implantable sensors.

For ease of illustration, the techniques presented are generally described herein with reference to the microphone 140(A) and the accelerometer 140(B). However, it is to be appreciated that an implantable tissue-stimulating prosthesis may also include other types of sensors, such as a telecoils, sensors for picking up nerve signals (e.g., an electroencephalogram (EEG)), etc. As such, the microphone 140(A) and the accelerometer 140(B) are merely illustrative of a number of different types of implantable sensors that may be affected by feedback from output channels, as described elsewhere herein.

In operation, the microphone 140(A) and the accelerometer 140(B) detect input (sound/vibration) signals (e.g., external acoustic sounds and/or body noises) and convert the detected input signals into electrical signals. These electrical signals are received by the signal processor 136, which is configured to execute signal processing and coding to convert the electrical signals into processed signals that represent the detected signals. The processed signals are then provided to the stimulator unit 138, which is configured to utilize the processed signals to generate electrical stimulation signals that are delivered to the recipient's cochlea via one or more of the intra-cochlear stimulating contacts 142(1)-142(22) implanted in the recipient's cochlea 116. In this way, cochlear implant 100 stimulates the recipient's auditory nerve cells, bypassing absent or defective hair cells that normally transduce acoustic vibrations into neural activity.

As noted above, cochlear implant 100 includes one or more electrical components positioned in the hermetic housing 129, as well as one or more electrical components located outside the hermetic housing 129. There is a need to enable electrical connections between various components outside of the hermetic housing 129 with various components within the housing 129. As such, the cochlear implant 100 includes a hermetic feedthrough 150 that provides a physical electrical connection that is used to transfer signals to/from the electrical components outside of the hermetic housing 129 to/from the electrical components within the hermetic housing 129. In FIG. 1B, conductors 152 extend from the hermetic feedthrough 150 to internal coil 130, microphone 140(A), accelerometer 140(B), reference contact 142(23), reference contact 142(24), and to each of the intra-cochlear stimulating contacts 142(1)-142(22). For ease of illustration, FIG. 1B illustrates only a subset of the intra-cochlear stimulating contacts 142(1)-142(22) and, accordingly, only a subset of the conductors 152 extending to the intra-cochlear stimulating contacts 142(1)-142(22).

The term "input channel" is used herein to refer to the combination of a sound input component/device and an associated conductor that connects the sound input component to another component (e.g., feedthrough wire). In the embodiments of FIGS. 1A and 1B, the microphone 140(A) and the accelerometer 140(B) are sound input components that are each associated with one or more conductors 152. As such, cochlear implant 100 includes two input channels, referred to as input channel 156(1) and input channel 156(2). Input channel 156(1) includes the microphone 140(A) and the associated conductor(s) 152 and input channel 156(2) includes the accelerometer 140(B) and the associated conductor(s) 152. As noted above, a tissue-stimulating prosthesis in accordance with embodiments presented herein may comprise additional or alternative input channels that include, for example, telecoils, sensors for picking up nerve signals, etc. As such, the input channels 156(1) and 156(2) are merely illustrative of a number of different types of implantable channels may be affected by feedback from output channels, as described elsewhere herein.

The term "output channel" is used herein to refer to the combination of a stimulation component/device and an associated conductor that connects the stimulation component to another component (e.g., feedthrough wire). In the embodiments of FIGS. 1A and 1B, the intra-cochlear stimulating contacts 142(1)-142(22), reference contact 142(23), and reference contact 142(24) are stimulation components each associated with one or more conductors 152. As such, cochlear implant 100 includes twenty-four (24) output channels 158(1)-158(24). The cochlear implant 100 also comprises twenty-four (24) outputs, namely intra-cochlear contacts 142(1)-142(22) and extra-cochlear contacts 142(23)-142(24). As such, cochlear implant 100 includes twenty-four output channels 158(1)-158(24), where each output channel is formed by a corresponding contact 142(1)-142(24) and one or more associated conductors 152.

Prior to implantation, the housing 129, the internal coil 130, the feedthrough 150, and at least a portion of the conductors 152 in proximity to the feedthrough 150 may be overmolded/encapsulated with a silicone elastomer to create a uniform compliant surface suitable for implantation. This encapsulation, which has been omitted from FIGS. 1A and 1B for ease of illustration, generally isolates the internal coil 130 and the conductors 152 in proximity to the feedthrough 150 from each other and from the implanted environment. That is, the encapsulation is generally resistant to the ingress of bodily fluid and has material properties that electrically isolate each of the conductors 152 and the internal coil 130.

A hermetic feedthrough, such as hermetic feedthrough 150, may be one of the most complex mechanical structures in an implantable medical device and are difficult to form properly. Hermetic feedthrough 150 includes an insulator 154 (e.g., formed from ceramic) and one or more conductors 153 (e.g., formed from platinum) that extend through the insulator. Due to the requirements of the manufacturing process, the conductors 153 extending through the insulator 154 are uninsulated and can comprise, or be joined to, the conductors 152. Therefore, at the outer surface of the hermetic feedthrough 150, only the applied encapsulation isolates the conductors 152 or 153.

As described in detail above, the cochlear implant 100 includes both implanted sound input components (e.g., microphone 140(A) and accelerometer 140(B)) as well as implanted stimulation components (e.g., intra-cochlear contacts 142(1)-142(22) and reference contacts 142(23)-142(24)). The sound input components are used to capture input signals (e.g., acoustic sounds, body noises, etc.), which in turn are used by the cochlear implant 100 to generate stimulation signals useable by the stimulation components to stimulate the recipient. That is, the cochlear implant 100 is a totally implantable device that is configured to: (1) detect/receive sounds from within the recipient, (2) process the sounds, and (3) generate stimulation signals for delivery to the recipient to evoke perception of the sound signals. As such, the use of the implantable sound input components provide the recipient with the ability to have a truly "invisible" prosthesis (i.e., since there are no external components, the prosthesis is invisible to others).

Although the use of the implanted sound input components facilitates the totally implantable nature of the implant, the present applicants have discovered that there is a potential for the creation of a feedback path between an output channel and an input channel, where "feedback" (i.e., a portion of the stimulation signals) will appear in the input channel. For example, a feedback path may be created between the stimulation components themselves (e.g., contacts 142(1)-142(24)) and the sound input components themselves (e.g., microphone 140(A) and accelerometer 140(B)) via the recipient's tissue/fluid. In other examples, fluid ingress (leakage) into the encapsulation at the feedthrough 150 can lead to the creation of conductive pathways between the conductors 152/153 connected to the sound input components and the conductors 152/153 connected to the stimulation components (i.e., the silicone encapsulation provides a high impedance insulation between the wires, but over time body fluids can leak under the silicone on the outside of the feedthrough and create a slightly conductive path between the stimulator wires and the microphone/accelerometer wires). In general, stimulation signals at the output channels have magnitudes that are significantly larger than the magnitudes of input signals on the input channels. That is, the output channels carry high voltage stimulation signals (e.g., up to the order of 10 Volts) while the input channels carry low voltage input signal wires (e.g., on the order of several millivolts). Due to this voltage difference, the feedback (i.e., a portion of the high voltage stimulation signals that pass through a feedback path to one or more input channels) will cause electrical interference within the one or more input channels. In certain embodiments, this electrical interference may be perceived by the recipient as audible noise.

In certain examples, it may not be possible to eliminate the feedback between an input and an output channel. However, the present applicants have also discovered that, since the feedback, and thus the resulting electrical interference, is the result of the stimulation signals generated by the cochlear implant 100, knowledge of the stimulation signals can be used to suppress the electrical interference.

More specifically, in the embodiment of FIGS. 1A and 1B, the cochlear implant 100 comprises the interference suppression module 135 (FIG. 1B). The interference suppression module 135 is configured to determine the presence of at least one feedback path between at least one of the output channels 158(1)-158(24) and at least one of the input channels 156(1)-156(2). For each output-to-input channel combination for which a feedback path is present, the interference suppression module 135 is configured to determine a "feedback transfer function" which characterizes the propagation of feedback that passes between the respective output and input channel. The interference suppression module 135 is configured to subsequently use the feedback transfer function to generate feedback compensation signals for application to the input channel. As described further below, in certain embodiments, the feedback transfer function is used to determine weights for a compensation filter that is applied to the respective output channel to generate the compensation signal for application to the input channel.

FIG. 1B illustrates the presence of any number of feedback paths 162 between output channel 158(22) and input channel 156(1). As noted, the interference suppression module 135 is configured to determine the presence of the feedback path(s) 162 and to determine a feedback transfer function for the feedback path(s) 162 (i.e., for the output-to-input channel combination comprised of output channel 158(22) and input channel 156(1)). Using the feedback transfer function (i.e., the determined characteristics of the feedback path(s) 162), the interference suppression module 135 is configured to calculate weights for a "feedback compensation filter" that can be used to subsequently generate feedback compensation at input channel 156(1). That is, once the characteristics of the feedback path 162 are known, the interference suppression module 135 can generate, in real-time, an estimate of the feedback that passes from the output channel 158(22) to the input channel 156(1). Given this estimate, the interference suppression module 135 can determine feedback compensation for application at the input channel 156(1), where the feedback compensation, when applied at the input channel 156(1), will cancel out the feedback that passes from the output channel 158(22) to the input channel 156(1).

Figure 2A:
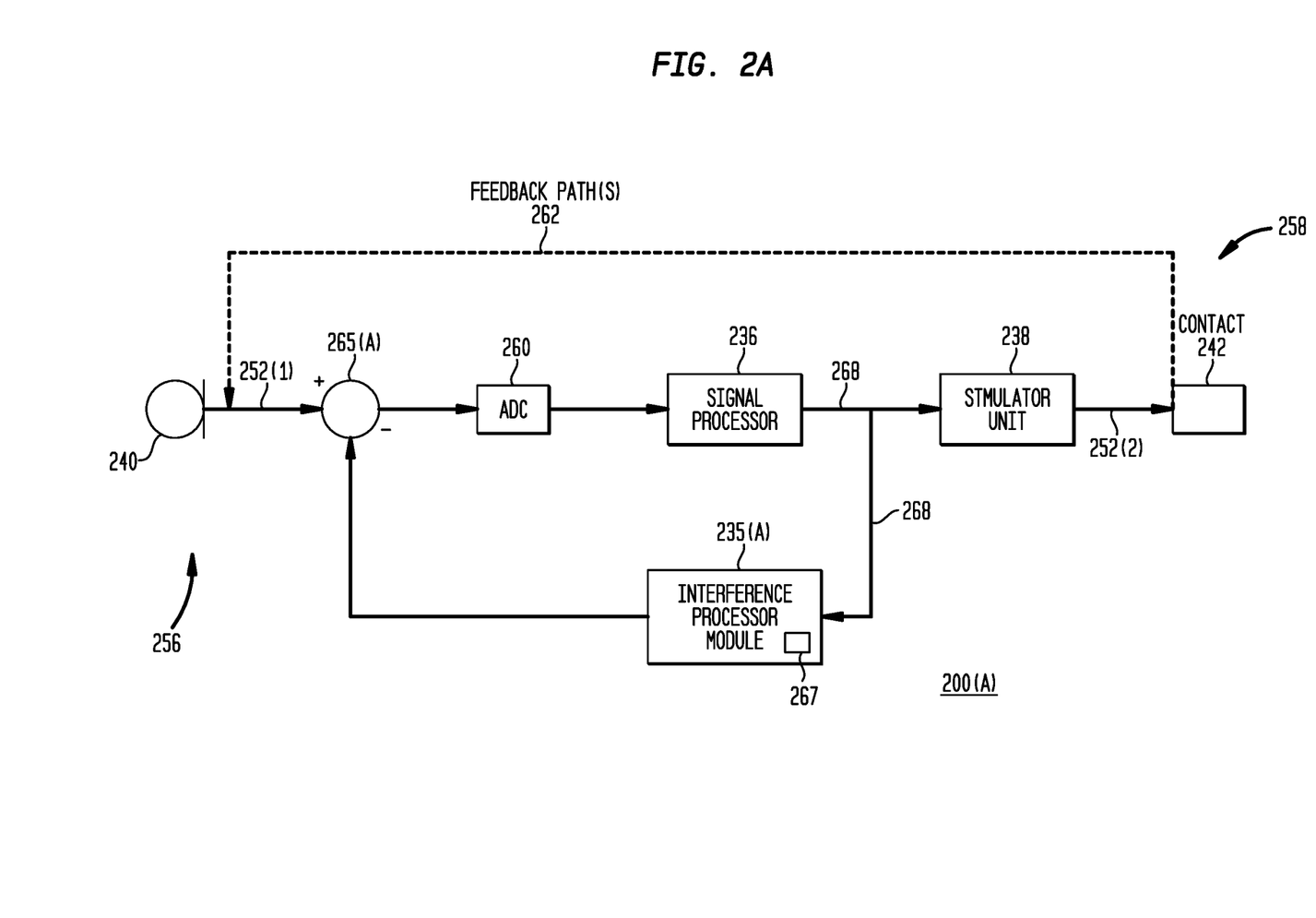
FIG. 2A is a schematic diagram illustrating interference suppression operations of a cochlear implant, in accordance with certain embodiments presented herein.
Figure 2B:
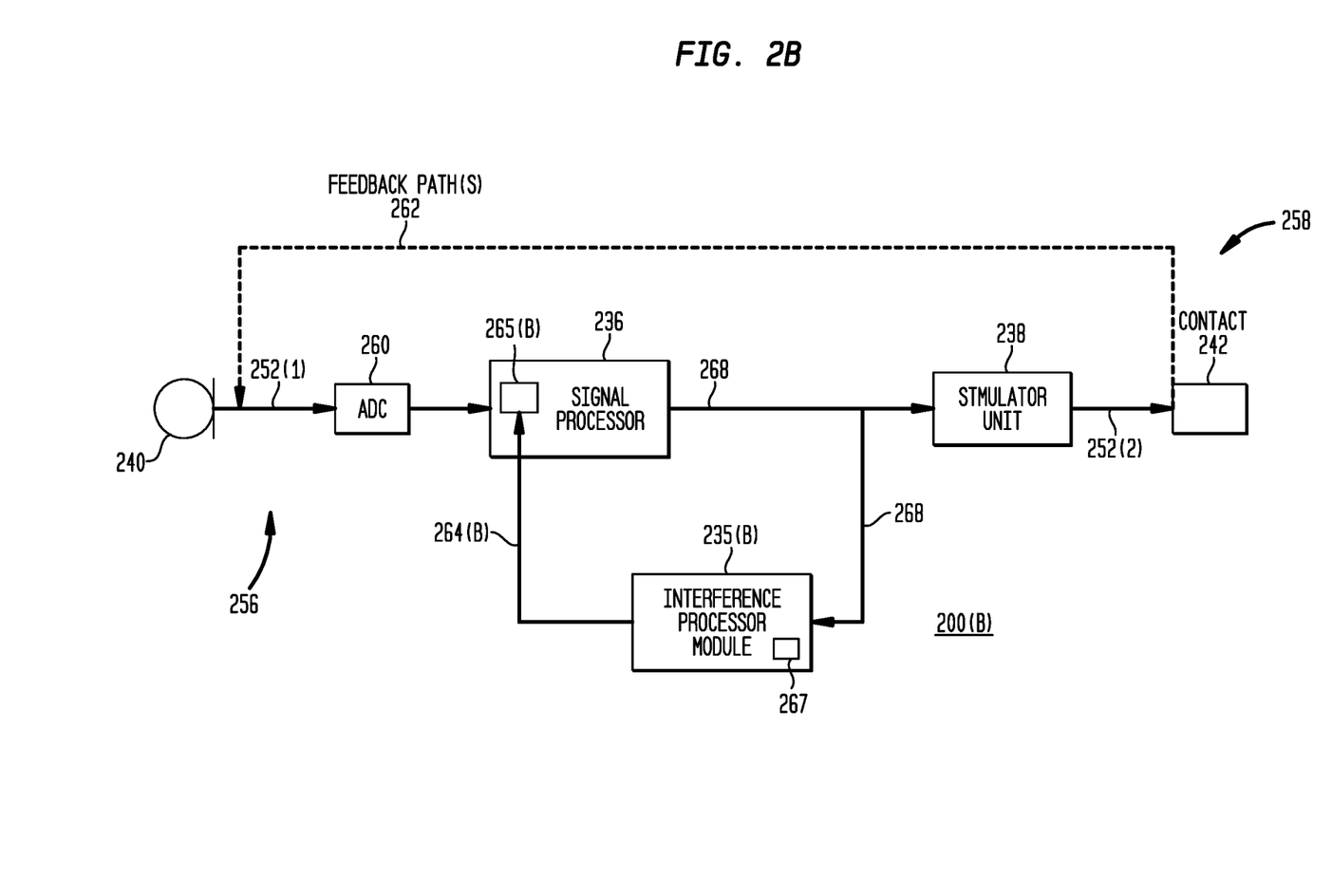
FIG. 2B is a schematic diagram illustrating interference suppression operations of a cochlear implant, in accordance with certain embodiments presented herein.

FIGS. 2A and 2B are simplified schematic block diagrams illustrating portions of two cochlear implants, referred to as cochlear implants 200(A) and 200(B), respectively, that are configured to implement interference suppression operations in accordance with examples presented herein. For ease of description, FIGS. 2A and 2B illustrate similar arrangements that include a single input channel 256 and a single output channel 258. However, as described elsewhere herein, certain embodiments of the present invention may be implemented with greater numbers of input channels and/or output channels.

The input channel 256 includes an implantable microphone 240 that is electrically connected to an Analog-to-Digital converter (ADC) 260 via an electrical path that includes a conductor 252(1). The implantable microphone 240 generates analog signals representative of detected sound signals and the ADC 260 converts the analog signals into the digital domain for use by a digital signal processor 236. The output channel 258 includes a stimulating contact 242 that is connected to a stimulator unit 238 via an electrical path that includes a conductor 252(2). In general, the output channel 258 carries stimulation signals from the stimulator unit 238 for delivery to the recipient via the stimulating contact 242.

As noted above, there is a potential for the creation of any number of feedback path(s) 262 to be created between the output channel 258 and the input channel 256 via, for example, the recipient's tissue, leakage at a feedthrough (e.g., a conductive path formed between conductors 252(1) and 252(2) as a result of fluid ingress into an encapsulation), etc. That is, a portion of the stimulation signals that are sent to the stimulating contact 262 via the output channel 258 will pass through the feedback path(s) 262 and, accordingly, will appear within the microphone signals on the input channel 256. The portion of the stimulation signals that pass through the feedback path(s) 262 is referred to herein as "output feedback" or, more simply, as "feedback." The feedback that passes through the feedback path(s) 262 may create electrical interference at the input channel 256.

As noted above, the cochlear implants 200(A) and 200(B) each include an ADC 260 that is configured to receive analog microphone signals via the input channel 256. The ADC 260 is configured to convert the analog microphone signals into digital microphone signals that are processed by the digital signal processor 236. FIG. 2A illustrates an example in which the interference suppression is performed in the analog domain, while FIG. 2B illustrates an example in which the interference suppression is performed in the digital domain.

Referring first to the specific embodiment of FIG. 2A, an interference suppression module 235(A) is provided to suppress the interference caused by the feedback path(s) 262. The interference suppression module 235(A) is configured to determine the presence of the feedback path(s) 262 and to determine a feedback transfer function 267 for the feedback path(s) 262 (i.e., determine an output-to-input transfer function between output channel 258 and input channel 256). The feedback transfer function 267 represents the characteristics (e.g., amplitude and phase) of the feedback path(s) 262.

Using the feedback transfer function 267, the interference suppression module 235(A) is configured to create an analog compensation filter 265(A) that models the feedback path voltage in response to current stimulation. The analog compensation filter 265(A) is configured to apply, to the analog microphone signals in the input channel 256, an analog compensation (e.g., an electric voltage signal) that is configured to cancel out the portion of the stimulation signals that pass through the feedback path(s) 262 and that appear in the input channel. As such, the interference suppression module 235(A) and/or the analog compensation filter 265(A) includes hardware (e.g., resistors, buffers, amplifiers, etc.) that generate an electric voltage that is combined with (e.g., subtracted from or added to) the analog microphone signals. As shown, the analog compensation is applied in the analog domain (i.e., before the ADC 260).

Referring next to the specific embodiment of FIG. 2B, an interference suppression module 235(B) is provided to suppress the interference caused by the feedback path(s) 262. Similar to the embodiment of FIG. 2A, the interference suppression module 235(B) is configured to determine the presence of the feedback path(s) 262 and to determine the feedback transfer function 267 for the feedback path(s) 262. Using the feedback transfer function 267, the interference suppression module 235(B) is configured to create a digital compensation filter 265(B) that models the feedback path(s) voltage in response to current stimulation. The digital compensation filter 265(B) is configured to apply, to the digital microphone signals in the input channel 256, a digital compensation that is configured to cancel out the portion of the stimulation signals that pass through the feedback path(s) 262 and that appear in the input channel. In FIG. 2B, the digital compensations are applied in the digital domain (i.e., after the ADC 260) by the digital signal processor 236.

Collectively, FIGS. 2A and 2B illustrate two different techniques for application of feedback compensation(s) configured to cancel out the portion of the stimulation signals that pass through the feedback path(s) 262 (i.e., in the analog or the digital domain). However, in both of the examples of FIGS. 2A and 2B, the feedback compensation(s) are generated based on a feedback transfer function 267, which generally represents one or more characteristics of the feedback path(s) 262, as well as the stimulation signals that are carried/delivered on output channel 258

More specifically, the signal processor 236 is configured to execute signal processing and coding to convert the electrical signals received from the microphone 240 into processed signals 268 that generally represent target acoustic sounds that were detected by the implantable microphone 240. The stimulator unit 238 is configured to receive the processed signals 268 from signal processor 236 and to utilize the processed signals 268 to generate electrical stimulation signals that are delivered to the recipient's cochlea via output channel 258 (i.e., via wire 252(2) and contact 242).

In the examples of FIGS. 2A and 2B, the processed signals 268 are not only delivered to the stimulator unit 238, but also to the interference suppression modules 235(A) and 235(B). The interference suppression modules 235(A) and 235(B) can use the information included in the processed signals 268, along with the feedback transfer function 267, to determine the real-time feedback compensations for application to the input channel 256 via the filters 265(A) or 265(B).

The feedback transfer function 267 may be produced/generated in a number of different manners, several examples of which are described below with specific reference to the arrangement of FIG. 2B. In certain examples, the feedback transfer function 267 is generated based on one or more measurements at the input channel 256 when there is no audio signal coming from the microphone 240. More specifically, in one example, the interference suppression module 235(B) identifies a low input period at input channel 256 (e.g., a time period in which the implantable microphone 240 is turned off and/or a time period when acoustic/vibration input is low). During the low input period, the interference suppression module 235(B) causes test stimulation to be delivered to the recipient via the output channel 258. In certain examples, in order to reduce disturbance to the recipient, the test stimulation can be delivered to the recipient below the recipient's hearing threshold (e.g., at a level that does not evoke a hearing perception by the recipient).

When the test stimulation is delivered, the interference suppression module 235(B) performs one or more measurements at the input channel 256 to determine the feedback signal (e.g., voltage) in the input channel. Since, as noted above, the test stimulation is delivered during a period of low acoustic/vibration input, the signal at the input channel can be attributed to feedback passing through feedback path(s) 262. The interference suppression module 235(B) is aware of the attributes (e.g., frequency) of the test stimulation and, given this knowledge, the interference suppression module 235(B) can determine the feedback transfer function 267. As noted, the feedback transfer function 267 generally represents the amplitude and phase changes that occur due to the feedback path(s) 262, which can vary across stimulation frequency.

It is to be appreciated that the above described technique for determination of the feedback transfer function 267 are illustrative and that other techniques may be utilized in accordance with embodiments presented herein. For example, in an additional embodiment, the feedback transfer function 267 may be determined by monitoring the input channel 256 over a period of time without waiting for a period of quiet.

In such an embodiment, the input channel data obtained from the input channel 256 over the period of time could be analyzed in view of stimulation signals delivered via the output channel 258 during the period of time to determine how the stimulation signals affected the input during the period of time. That is, knowledge of the stimulation signals during the period of time can be used to determine how the input channel 256 is impacted by feedback from the output channel 258. This can be determined because the feedback is inherently related to the stimulation rate, not the input signal, and therefore it is possible to detect. It is also unlikely that an acoustic input signal with the same properties would co-exist with the feedback signal.

In addition, the feedback transfer function 267 could be estimated and updated periodically, continuously, etc. However, in practice, it is likely that the periods would be restricted to times when it is known that the signal is related to feedback, as opposed to mixing with a similar real input signal.

Once the feedback transfer function 267 is calculated by the interference suppression module 235(B), the interference suppression module 235(B) can use the feedback transfer function 267 in real-time to compensate for feedback passing through feedback path(s) 262. That is, the feedback compensation filter 265(B) represents the predetermined characterizations of the feedback that can be used along with knowledge of the attributes of the stimulation signals (e.g., the frequency of the stimulation signals) to generate and deliver compensation signals.

The above illustrates several techniques for calculation of a feedback transfer function 267 and associated compensation filter design. In certain embodiments, the feedback transfer function 267 and the associated digital compensation filter 265(B) may be adjusted based on iterative measurements of the feedback received at the input channel 256. This could be achieved using, for example, an adaptive least mean squares (LMS) technique. An example of such an arrangement is shown in FIG. 3.

Figure 3:
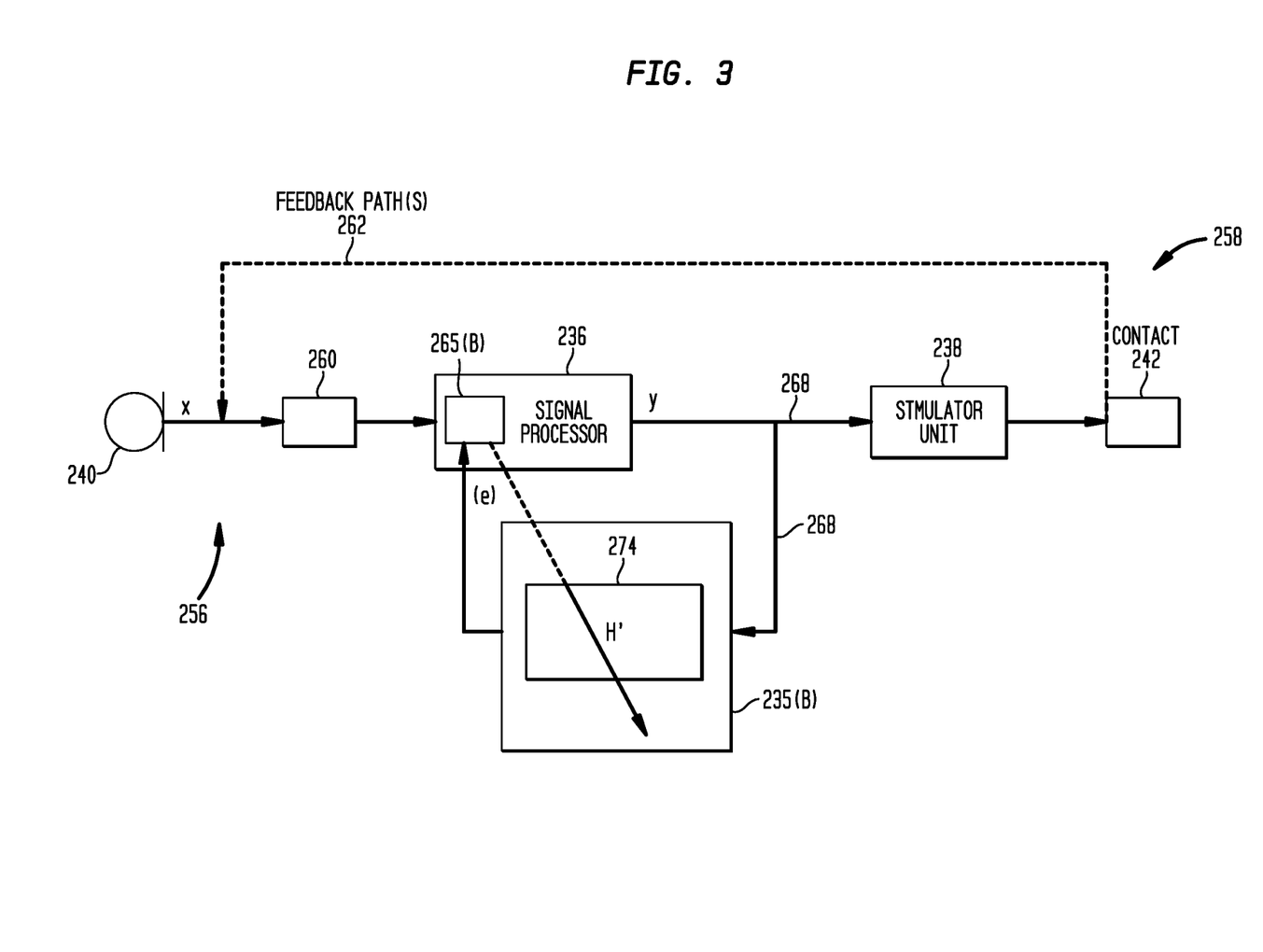
FIG. 3 is a schematic diagram illustrating determination of compensation filter weights, in accordance with certain embodiments presented herein.

More specifically, FIG. 3 is a schematic diagram illustrating operations of the cochlear implant 200(B) during measurement of the feedback between output channel 258 and input channel 256. In this example, the transfer function estimate (H'), for the filter 265(B) is using, for example, the techniques described above. As shown, in this example the interference suppression module 235(B) includes an adaptive LMS filter 274 that is used to update the feedback transfer function 267 (H') during the measurement procedure. The feedback transfer function 267 is adjusted by minimizing the mean square error of the signal (e). By minimizing the mean square error of the signal (e), the adaptive LMS filter 274 estimates the transfer function between signal Y and signal X, which is the feedback of the feedback path(s) 262 plus the digital to analog current conversion at stimulator unit 238.

It is to be appreciated that the use of LMS is one example technique for updating compensation filter weights and that a number of other procedures for estimating the feedback path transfer function may be implemented in accordance with embodiments presented herein.

The above examples have, for ease of illustration, been primarily described with reference to interference suppression module 235(A) of FIG. 2A. It is to be appreciated that similar operations may be implemented at interference suppression module 235(B) to generate weights for feedback compensation filter 265(B). However, since FIGS. 2A and 2B illustrate analog and digital compensations, respectively, it is also to be appreciated that the feedback compensation filters 265(A) and 265(B) may be implemented differently and that the corresponding compensations manner may be differ in each of the analog and digital examples.

In addition, also for ease of illustration, the above examples have been described with reference to a single output-to-input channel combination. In practice, an implantable auditory prosthesis or other implantable medical device may include multiple output channels and multiple input channels and, accordingly, multiple output-to-input channel combinations. In certain embodiments, a different compensation filter, each operating differently, may be generated, as described above, for each output-to-input channel combination or at least for each output-to-input channel combination for which one or more feedback paths exist.

For example, referring back to the arrangement of FIGS. 1A and 1B, the cochlear implant 100 includes two inputs, namely microphone 140(A) and accelerometer 140(B) both implanted in the recipient and connected to the feedthrough via a wire 152. As such, cochlear implant 100 includes two input channels 156(1) and 156(2). The cochlear implant 100 also comprises twenty-four (24) outputs, namely intra-cochlear contacts 142(1)-142(22) and extra-cochlear contacts 142(23)-142(24). As such, cochlear implant 100 includes twenty-four output channels 158(1)-158(24), where each output channel is formed by a corresponding contact 142(1)-142(24) and a wire 152.

There is a possibility that feedback paths could be created between any of the twenty-four output channels 158(1)-158(24) and either of the input channels 156(1) and 156(2), thus possibility leading to a maximum of forty-eight (48) output-to-input channel combinations and accordingly, a possible maximum of forty-eight feedback path transfer functions. The interference suppression module 135 may perform the operations described above with reference to FIGS. 2A, 2B, and/or 3 to generate feedback transfer functions and compensation filters for all or a subset of the forty-eight output-to-input channel combinations. The generation of feedback transfer functions and filters for each of a plurality of output-to-input channel combinations may be, in certain examples, a sequential (channel by channel) process as described above.

In certain embodiments, the compensation filters for a plurality of output-to-input channel combinations may each be different and specific to the associated output-to-input channel combinations. However, in other embodiments, the interference suppression module 135 may determine that a plurality (e.g., a subset or all) of the forty-eight output-to-input channel combinations may have similar feedback paths with similar feedback transfer functions. That is, through a measurement process, the interference suppression module 135 determines that each of the plurality of output-to-input channel combinations generates a similar amount of feedback at the corresponding input channel. In these embodiments, since the feedback is similar for each of the output-to-input channel combinations, the interference suppression module 135 may use the same compensation filter to generate compensation signals for all of the plurality of the output-to-input channel combinations.

As noted elsewhere herein, feedback path(s) between an output and input channel in an implantable auditory prosthesis or other implantable medical device may be the result of any of a number of different causes (e.g., via the recipient's tissue/fluid, fluid ingress into encapsulation of the device, etc. or combination thereof). However, it is also possible for implantable input and output channels to exist without the presence of feedback path(s) there between. As such, in certain embodiments, the instantiation of a feedback compensation filter for an output-to-input channel combination may occur only after the detection of feedback at the corresponding input channel. For example, again referring to the example of FIGS. 1A and 1B, the interference suppression module 135, signal processor 136, and/or another element of cochlear implant 100 may be configured to monitor (e.g., periodically) the input channels 156(1) and 156(2) for potential feedback. The feedback from an output channel 158(1)-158(24) creates interference that, in certain examples, may be identified as predetermined/known noise patterns in the input channel. Therefore, in certain embodiments, the cochlear implant 100 is configured to monitor (e.g., periodically) the input channels 156(1) and 156(2) for noise that is likely attributable to (i.e., the result of) feedback from one or more of the output channels 158(1)-158(24).

In other embodiments, the cochlear implant 100 may be configured to periodically (e.g., such as once per day, once per week, etc.) initiate a feedback evaluation process to determine whether feedback is present between any of the output-to-input channel combinations. In these embodiments, the cochlear implant 100 can evaluate (e.g., sequentially) each of the forty-eight output-to-input channel combinations to determine whether feedback is present (e.g., the cochlear implant 100 may perform the operations described above with reference to FIGS. 2A, 2B, and/or 3 to measure feedback at a given input channel 156(1) or 156(2), that is caused by a given output channel 158(1)-158(24)).

Once the cochlear implant 100 determines that feedback is likely present at one or more of the input channels 156(1) or 156(2), the cochlear implant 100 can initiate a process to determine which of the output channel(s) 158(1)-158(24) is/are the source of the feedback and, accordingly, determine a feedback transfer function for the specific output-to-input channel combination(s) which, in turn, can be used as part of a feedback compensation filter for the specific output-to-input channel combination(s).

Once a compensation filter is instantiated for an output-to-input channel combination, the filter may be periodically re-evaluated and adjusted, as needed. This process may be similar to the processes described with reference to FIGS. 2A, 2B, and/or 3 for the determination of the initial filter weights. In certain embodiments, the filter re-evaluation process may be performed periodically, such as once per day, once per week, etc. In other embodiments, the filter re-evaluation process may be performed in response to a triggering event, such as the detection of additional electrical interference (e.g., noise) at an input channel 156(1)-156(2).

In one example embodiment that makes use of an LMS adaptive filter, the LMS could update continuously, even under conditions of acoustic input. This may be regulated and adaption may only be allowed when conditions are favorable to do so (e.g., low acoustic input level). In certain such examples, an aspect is to determine if the signal is due to feedback or due to another acoustic input. As noted above, this can be determined because the feedback is inherently related to the stimulation rate, not the input signal, and therefore possible detect. It is also unlikely that an acoustic input signal with the same properties would co-exist with the feedback signal.

Figure 4A:
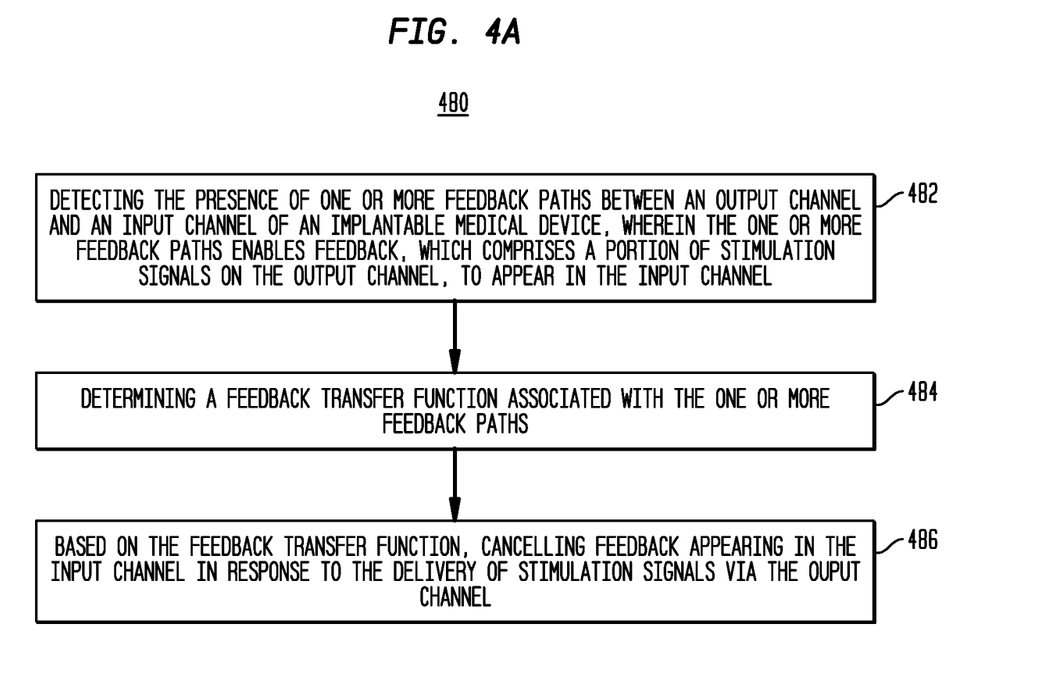
FIG. 4A is a flowchart of an interference suppression method, in accordance with certain embodiments presented herein.

FIG. 4A is a flowchart of a method 480 in accordance with embodiments presented herein. Method 480 begins at 482 where an implantable medical device detects the presence of one or more feedback paths between an output channel and an input channel of the implantable medical device, wherein the one or more feedback paths enables feedback, which comprises a portion of stimulation signals on the output channel, to appear in the input channel. At 484, the implantable medical device determines a feedback transfer function associated with the one or more feedback paths. At 486, based on the feedback transfer function, the implantable medical device cancels feedback appearing in the input channel in response to the delivery of stimulation signals via the output channel.

Figure 4B:
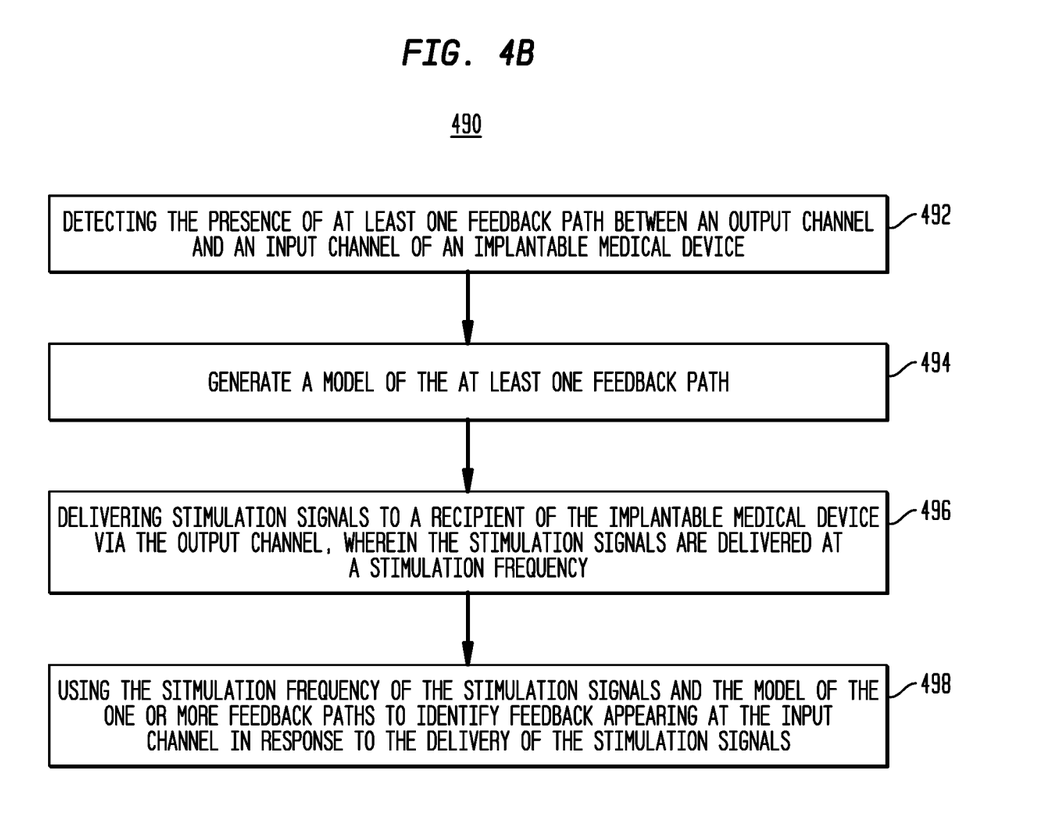
FIG. 4B is a flowchart of another interference suppression method, in accordance with certain embodiments presented herein.

FIG. 4B is a flowchart of a method 490 in accordance with embodiments presented herein. Method 490 begins at 492 where an implantable medical device detects the presence of at least one feedback path between an output channel and an input channel of an implantable medical device. At 494, the implantable medical device generates a model of the at least one feedback path. At 496, the implantable medical device delivers stimulation signals to a recipient of the implantable medical device via the output channel, wherein the stimulation signals are delivered at a stimulation frequency. At 498, the implantable medical device uses the stimulation frequency of the stimulation signals and the model of the one or more feedback paths to identify feedback appearing at the input channel in response to the delivery of the stimulation signals.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A tissue-stimulating prosthesis, comprising:
at least one input channel including an implantable sensor and one or more associated conductors configured to be implanted in a recipient;
at least one output channel including an electrical stimulation component and one or more associated conductors configured to be implanted in the recipient; and
an interference suppression module configured to:
detect, on the at least one input channel, electrical interference generated by the at least one output channel via at least one electrically conductive path extending through at least one of bodily fluid or body tissue of the recipient, and
determine real-time compensation for application at the at least one input channel, wherein application of the real-time compensation is configured to cancel the electrical interference at the at least one input channel.

2. The tissue-stimulating prosthesis of claim 1, wherein the interference suppression module is configured to determine one or more characteristics of the at least one electrically conductive path, and wherein the interference suppression module is configured to determine the real-time compensation based on one or more attributes of electrical stimulation signals that are to be delivered to the at least one output channel and based on the one or more characteristics of the at least one electrically conductive path.

3. The tissue-stimulating prosthesis of claim 2, wherein the interference suppression module is configured to use the one or more characteristics of the at least one electrically conductive path to generate, in real-time, an estimate of a portion of electrical stimulation signals delivered via the at least one output channel that passes from the at least one output channel to the at least one input channel in response to delivery of the electrical stimulation signals via the at least one output channel, wherein the portion of the electrical stimulation signals causes the electrical interference at the at least one input channel.

4. The tissue-stimulating prosthesis of claim 2, wherein to determine one or more characteristics of the at least one electrically conductive path, the interference suppression module is configured to:
deliver test stimulation via the at least one output channel during a low input period at the at least one input channel; and
in response to delivery of the test stimulation via the at least one output channel, perform at least one measurement at the input channel.

5. The tissue-stimulating prosthesis of claim 4, wherein the interference suppression module is configured to:
iteratively deliver sets of test stimulation via the at least one output channel;

in response to delivery of each iterative set of test stimulation via the output channel, performing an additional at least one measurement at the input channel; and in response to each additional at least one measurement, iteratively updating the one or more characteristics of the at least one electrically conductive path.

6. The tissue-stimulating prosthesis of claim 2, wherein to determine one or more characteristics of the at least one electrically conductive path, the interference suppression module is configured to:

monitor the input channel for a period of time to capture input channel data; and analyzing the input channel data captured for the period of time in view of electrical stimulation signals delivered via the output channel during the period of time.

7. The tissue-stimulating prosthesis of claim 1, wherein the electrical stimulation component comprises a stimulating contact configured to deliver electrical stimulation signals to a recipient.

8. The tissue-stimulating prosthesis of claim 1, wherein the implantable sensor comprises an implantable microphone.

9. A method, comprising:

detecting a presence of one or more electrically conductive paths between an output channel that delivers electrical stimulation signals to a recipient and an input channel of an implantable medical device, wherein the one or more electrically conductive paths extend through one or more of tissue or fluid of the recipient and enable a portion of the electrical stimulation signals on the output channel to appear as electrical interference in the input channel;

determining at least one transfer function associated with the one or more electrically conductive paths, wherein the at least one transfer function characterizes a propagation of the portion of the electrical stimulation signals that pass between the output channel and the input channel; and using the transfer function to cancel the electrical interference appearing in the input channel in response to delivery of electrical stimulation signals via the output channel.

10. The method of claim 9, further comprising:

delivering a first set of electrical stimulation signals via the output channel; and determining a frequency of the first set of electrical stimulation signals;

wherein cancelling the electrical interference appearing in the input channel in response to delivery of electrical stimulation signals via the output channel comprises:

using the frequency of the first set of electrical stimulation signals to generate one or more compensations for the input channel; and applying the one or more compensations to cancel, from the input channel, the electrical interference that is likely to be present in the input channel as a result of the first set of electrical stimulation signals.

11. The method of claim 9, wherein determining a transfer function associated with the one or more electrically conductive paths includes:

delivering test stimulation via the output channel during a low input period at the input channel; and in response to delivery of the test stimulation via the output channel, performing at least one measurement at the input channel.

12. The method of claim 11, further comprising:

iteratively delivering sets of test stimulation via the output channel;

in response to delivery of each iterative set of test stimulation via the output channel, performing an additional at least one measurement at the input channel; and in response to each additional at least one measurement, iteratively updating the transfer function.

13. The method of claim 9, wherein determining a transfer function associated with the one or more electrically conductive paths includes:

monitoring the input channel for a period of time to capture input channel data; and analyzing the input channel data captured for the period of time in view of stimulation signals delivered via the output channel during the period of time.

14. The method of claim 9, wherein detecting the presence of one or more electrically conductive paths between an output channel and an input channel comprises:

monitoring the input channel for noise that is likely attributable to the portion of the electrical stimulation signals that pass between the output channel and the input channel.

15. The method of claim 14, wherein monitoring the input channel for the noise comprises:

monitoring the input channel for a presence of one or more predetermined noise patterns.

16. The method of claim 9, wherein the implantable medical device comprises a plurality of output channels and a number of input channels, and wherein the method further comprises:

detecting that a plurality of the number of input channels are each affected by a group of one or more electrically conductive paths extending from one or more of the plurality of output channels; and determining a transfer function for each group of one or more electrically conductive paths affecting one of the plurality of the number of input channels.

17. The method of claim 9, wherein the implantable medical device is an implantable auditory prosthesis and wherein the input channel includes a sound input component and one or more associated conductors and the output channel includes a stimulation component and one or more associated conductors.

18. The method of claim 9, wherein determining a transfer function associated with the one or more electrically conductive paths comprises:

generating a model of the one or more electrically conductive paths;

delivering electrical stimulation signals to a recipient of the implantable medical device via the output channel, wherein the electrical stimulation signals are delivered at a stimulation frequency; and using the stimulation frequency of the electrical stimulation signals and the model of the one or more electrically conductive paths to identify the electrical interference at the input channel in response to delivery of the electrical stimulation signals.

19. The method of claim 18, wherein cancelling the electrical interference appearing in the input channel in response to delivery of stimulation signals via the output channel, comprises:

determining real-time compensation for application at the input channel, wherein application of the real-time compensation is configured to cancel the electrical interference at the input channel.

20. The method of claim 18, wherein generating a model of the one or more electrically conductive paths comprises:
   delivering test stimulation via the output channel during a low input period at the input channel; and
   in response to delivery of the test stimulation via the output channel, performing at least one measurement at the input channel.

21. The method of claim 20, further comprising:
   iteratively delivering sets of test stimulation via the output channel;
   in response to delivery of each iterative set of test stimulation via the output channel, performing an additional at least one measurement at the input channel; and
   in response to each additional at least one measurement, iteratively updating the model of the one or more electrically conductive paths.

22. The method of claim 18, wherein generating a model of the one or more electrically conductive paths comprises:
   monitoring the input channel for a period of time to capture input channel data; and
   analyzing the input channel data captured for the period of time in view of electrical stimulation signals delivered via the output channel during the period of time.

23. An implantable medical device method, wherein the implantable medical device comprises at least one input channel and at least one output channel configured to carry input signals and electrical stimulation signals, respectively, the method comprising:
   delivering the electrical stimulation signals to a recipient of the implantable medical device via the at least one input channel;
   detecting, at the at least one input channel, electrical interference resulting from delivery of the electrical stimulation signals to the recipient via the at least one output channel to the at least one input channel, wherein electrical interference comprises a portion of the electrical stimulation signals;
   determining compensation for application at the at least one input channel; and
   applying the compensation at the at least one input channel to cancel the electrical interference resulting from delivery of the electrical stimulation signals to the recipient.

24. The implantable medical device method of claim 23, wherein the portion of the electrical stimulation signals pass from the at least one output channel to the at least one input channel via one or more electrically conductive pathways through one or more of bodily fluid or body tissue of the recipient, and wherein the method further comprises:
   determining a transfer function associated with the one or more electrically conductive paths, wherein the transfer function characterizes a propagation of the portion of the electrical stimulation signals that pass between the output channel and the input channel; and
   determining the compensation based on the transfer function and one or more attributes of the electrical stimulation signals.

25. The implantable medical device method of claim 24, wherein determining a transfer function associated with the one or more electrically conductive paths comprises:
   delivering test stimulation via the output channel during a low input period at the input channel; and
   in response to delivery of the test stimulation via the output channel, performing at least one measurement at the input channel.

26. The method of claim 25, further comprising:
   iteratively delivering sets of test stimulation via the output channel;
   in response to delivery of each iterative set of test stimulation via the output channel, performing an additional at least one measurement at the input channel; and
   in response to each additional at least one measurement, iteratively updating the transfer function.

27. The method of claim 24, wherein determining a transfer function associated with the one or more electrically conductive paths includes:
   monitoring the input channel for a period of time to capture input channel data; and
   analyzing the input channel data captured for the period of time in view of stimulation signals delivered via the output channel during the period of time.

28. The method of claim 23, wherein detecting electrical interference resulting comprises:
   monitoring the input channel for noise that is likely attributable to the portion of the electrical stimulation signals from the output channel.

29. The method of claim 28, wherein monitoring the input channel for noise comprises:
   monitoring the input channel for a presence of one or more predetermined noise patterns.

* * * * *